US006891077B2

(12) United States Patent
Rothwell et al.

(10) Patent No.: US 6,891,077 B2
(45) Date of Patent: May 10, 2005

(54) FIBRINOGEN BANDAGES AND ARTERIAL BLEEDING MODELS AND METHODS OF MAKING AND USING THEREOF

(75) Inventors: Stephen W. Rothwell, Columbia, MD (US); Chitra Krishnamurti, Potumac, MD (US); Thomas J. Reid, III, Rockville, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 166 days.

(21) Appl. No.: 10/202,650

(22) Filed: Jul. 25, 2002

(65) Prior Publication Data

US 2003/0040692 A1 Feb. 27, 2003

Related U.S. Application Data

(60) Provisional application No. 60/307,355, filed on Jul. 25, 2001.

(51) Int. Cl.[7] ............................................... A61F 13/00
(52) U.S. Cl. ........................... 602/48; 602/41; 424/443; 424/445
(58) Field of Search ................................. 424/443–449; 602/41–59; 604/304–308

(56) References Cited

U.S. PATENT DOCUMENTS

| 4,442,655 A | * | 4/1984 | Stroetmann | 53/428 |
| 4,600,574 A | * | 7/1986 | Lindner et al. | 424/448 |
| 5,047,249 A | * | 9/1991 | Rothman et al. | 424/543 |
| 5,451,509 A | * | 9/1995 | Speck | 435/13 |
| 5,700,634 A | * | 12/1997 | Speck | 435/4 |
| 5,709,889 A | * | 1/1998 | Speck | 424/617 |
| 2003/0175327 A1 | * | 9/2003 | Cochrum et al. | 424/445 |

OTHER PUBLICATIONS

Speck, R., et al. (1998) "Proposed Procedure for Evaluating Platelet Concentrate Units to Be Used for Transfusion" Clin Appl Thrombosis/Hemostasis, 4(3):217–219.

Neiva, T.J.C., et al. (1997) "Aluminum Induces Lipid Peroxidation and Aggregation of Human Blood Platelets" Brazilian Journal of Med and Bio Research, 30:599–604.

Glick, R., et al. (1981) "High Dose ε–Aminocaproic Acid Prolongs the Bleeding Time and Incsreases Rebleeding and Intraoperative Hemorrhage in Patients with Subarachnoid Hemorrhage" Neurosurgery, 9(4):398–401.

Green, D., et al. (1985) "Clinical and Laboratory Investigation of the Effects of ε–aminocaproic Acid on Hemostais" Journal of Laboratory and Clinical Medicine, 105(3):321–327.

Pierre, J., et al. (1999) "Tissue Factor Pathway Inhibitor Attenuates Procoagulant Activity and Upregulation of Tissue Factor at the Site of Balloon–Induced Arterial Injury in Pigs" Arterioscler Thromb Vasc Biol., 19:2263–2268.

Edwards, R. and Rickles, F. (1984) "Macrophage Procoagulants" Progress in Hemostatis and Thrombosis, pp. 183–209.

Greczy, Carolyn (1984) "Induction of Macrophage Procoagulant by Products of Activated Lymphocytes" Haemostasis 14:400–411.

(Continued)

Primary Examiner—Kim M. Lewis
(74) Attorney, Agent, or Firm—Elizabeth Arwine

(57) ABSTRACT

Disclosed herein are wound dressings comprising fibrinogen and at least one procoagulant such as propyl gallate in a therapeutic amount. Also disclosed are methods of treating wounds, increasing an amount of or rate of coagulation of blood from a wound, increasing an amount of or rate of clot formation over a wound, increasing blood platelet counts, activating a coagulation system, increasing the plasma concentration of fibrinogen, and decreasing the activated partial thromboplastin time. Also disclosed are an arterial bleeding model and methods of studying arterial bleeding.

17 Claims, 5 Drawing Sheets

OTHER PUBLICATIONS

Morey, A., et al. (2001) "Treatment of Grade 4 Renal Stab Wounds with Absorbable Fibrin Adhesive Bandage in a Porcine Model" Journal of Urology, 165:955–958.

Holcomb, J., et al. (1999) "Effect of Dry Fibrin Sealant Dressings versus Gauze Packing on Blood Loss in Grade V Liver Injuries in Resuscitated Swine" Journal of Trauma: Injury, Infection and Critical Care, 46(1):49–57.

Holcomb, J. et al. (1999) "Dry Fibrin Sealant Dressings Reduce Blood Loss, Resuscitation Volume, and Improve Survival in Hypothermic Coagulopathic Swine with Grade V Liver Injuries" Journal of Trauma, 47(2):233–242.

Ochsner, M., et al. (1990) "Fibrin Glue as a Hemostatic Agent in Hepatic and Splenic Trauma" Journal of Trauma, 30(7):884–887.

Larson, M., et al. (1995) "Efficacy of a Fibrin Hemostatic Bandage in Controlling Hemorrhage from Experimental Arterial Injuries" Arch. Surg., 130:420–422.

Suzuki, Y., et al. (1995) "Fibrin Glue Sealing for the Preventing of PAncreatic Fistulas Followinng Distal Pancreatectomy" Archives of Surgery, 130(9):952–955.

Pusateri, A., et al. (2001) "Effect of Fibrin Bandage Fibrinogen Concentration on Blood Loss after Grade V Liver Injury in Swine" Military Medicine, 166(3):217–222.

Cornum, R., et al. (2000) "Does the Absorbable Fibrin Adhesive Bandage Facilitate Partial Nephrectomy?" The Journal of Urology, 164(3):864–867.

Jackson, M. et al. (1997) "Hemostatic Efficacy of a Fibrin Sealant–based Topical Agent in a Femoral Artery Injury Model: A Randomized, blinded, placebo–controlled Study" Journal of Vascular Surgery, 26(2):274–280.

Holcomb, J., et al. (1998) "Efficacy of a Dry Fibrin Sealant Dressing For Hemorrhage Control After Ballistic Injury" Archives of Surgery, 133(1):32–35.

Cornum, R., et al. (1999) "Intraoperative Use of the Absorbable Fibrin Adhesive Bandage: Long Term Effects" Journal of Urology, 162(5):1817–1824.

Jackson, M., et al. (1999) "Fibrin Sealant in Preclinical and Clinical Studies" Current Opinion in Hematology, 6(6):415–422.

Duchesne, B., et al. (2001) "Use of Human Fibrin Glue and Amniotic Membrane Transplant in Corneal Perforation" Cornea, 20(2):230–232.

Parker, S. et al. (1999) "Fibrinogen–impregnated Collagen as a Combined Haemostatic Agent and Antibiotic Delivery System in Porcine Model of Splenic Trauma" Eur J Surg, 165(6):609–614.

Rothwell, S., et al. (2003) "Addition of a Propyl Gallate–based Procoagulant to a Fibrin Bandage Improves Hemostatic Performance in a Swine Arterial Bleeding Model" Thrombosis Research, 103:335–340.

Rothwell, S., et al. (2003)"ε–Amino Caproic Acid Additive Decreases Fibrin Bandage Performance in a Swine Arterial Bleeding Model" Thrombosis Research, 108:341–345.

Xiao, H.Y., et al. (2000) "Generation of Annexin V–positive Platelets and Shedding of Microparticles with Stimulus–dependent Procoagulant Activity During Storage of Platelets at 4°C" Transfusion, 40(4):420–427.

Lebowitz, R., et al. (1995) "Autologous Fibrin Glue in the Prevention of Cerebrospinal Fluid Leak Following Acoustic Neuroma Surgery" The American Journal of Otology, 16(2):172–174.

Holcomb, J., et al. (1997) "Implications of New Dry Fibrin Sealant Technology for Trauma Surgery" Surgical Clinics of North America, 77(4):944–952.

Rousou, J., et al. (1989) "Randomized Clinical Trial of Fibrin Sealant in Patients Undergoing Resternotomy or Reoperation After Cardiac Operations" J. Thorac Cardiovasc Surg, 97:194–203.

Matthew, T., et al. (1990) "Four Years' Experience With Fibrin Sealant in Thoracic and Cardivascular Surgery" 50:40–44.

Czerny, M., et al. (2000) "Collagen Patch Coated With Fibrin Glue Components " The Journal of Cardiovascular Surgery, 41(4):553–557.

Reddy, M., et al. (2002) "A Clinical Study of a Fibrinogen–Based Collagen Fleece for Dural Repair in Neurosurgery" Acta Neurochirurgica, 144:265–269.

Agus, G.B., et al. (1996) "Hemostatic Efficacy and Safety of TachoComb in Surgery: Ready to USe and Rapid Hemostatic Agent" Int Surg 81:316–319.

Galajda, Z., et al. (2002) "Subacute Left Ventricular Rupture Complicated by Free Wall Rupture: Repair with a TachoComb Sheet and Tissucol Glue" The Journal of Thoracic and Cardiovascular Surgery, 1235): 4 pages.

Cerwencka, H., et al. (1998) "Massive Liver Haemorrhage and Rupture Caused by HELLP–syndrome Treated by Collagen Fleeces Coated with Fibrin Glue" Eur J. Surg, 164:709–711.

Hollaus, P., et al. (1994) "The Use of Tachocomb inThoracic Surgery" J. Cardiovasc Surg, 35(6):169–170.

Scheyer, M., et al. (1996) "Tachocomb used in in Endoscopic Surgery" Surgical Endoscopy, 10:501–503.

Lerner, R. and Binur, N. (1990) "Current Status of Surgical Adhesives" Journal of Surgical Research, 48:165–181.

Katsuaki, O., et al. "Experimental Evaluation of Photocrosslinkable Chitosan as a Biologic Adhesive with Surgical Applications" Surgery, 130(5):844–850.

Dachary–Prigent, J., et al. (1996) "Physiopathological Significance of Catalytic Phospholipids in the Generation of Thrombin" Seminars in Thrombosis and Hemostasis, 22(2):157–164.

Hemker, H.C., et al. (1983) "Platelet Membrane Involvement in Blood Coagulation" Blood Cells, 9:303–317.

Ortel, T., et al. (1994) "Topical Thrombin and Acquired Coagulation Factor Inhibitors: Clinical Spectrum and Laboratory Diagnosis" American Journal of Hematology, 45:128–135.

Phillips, Steven (2000) "Physiology of Wound Healing and Surgical Wound Care" ASAIO Journal, 46:S2–S5.

(1999) "Amicar (Amnincaproic Acitd)" http://micro.magnet.fsu.edu/pharmaceuticals/pages/amicar.html. 1 page.

Anema, J.G., et al. (2001) "Potential Uses of Absorbable Fibrin Adhesive Bandage for Genitourinary Trauma" World J. Surg., 25:1573–7, Abstract.

Tsuki, H. et al. (2002)"Surgical Repair of Left Ventricular Free Wall Rupture Uing Layered Fibrin Glue Sheet and Fibrin Glue; Report of a case" Kyobu Geka, 55(10):887–890, Abstract.

* cited by examiner

FIBRINOGEN BANDAGES AND ARTERIAL BLEEDING MODELS AND METHODS OF MAKING AND USING THEREOF

CROSS REFERENCE TO RELATED APPLICATIONS

This application claims the benefit of U.S. Provisional Application Ser. No. 60/307,355, filed 25 Jul. 2001, naming Stephen J. Rothwell, Chitra Krishnamurti, and Thomas J. Reid, III, as joint inventors, which is herein incorporated by reference in its entirety.

ACKNOWLEDGMENT OF GOVERNMENT SUPPORT

This invention was made by employees of the United States Army. The government has rights in the invention.

BACKGROUND OF THE INVENTION

1. Field of the Invention

This invention relates generally to fibrinogen bandages and arterial bleeding models and methods of making and using thereof. In particular, the present invention relates to a fibrinogen bandage having propyl gallate and a swine arterial bleeding model.

2. Description of the Related Art

The control of hemorrhage is the initial step in first aid and field trauma care. Although the basic approach to homeostasis has not changed significantly since the onset of modem medicine, new and more effective methods, such as fibrinogen dressings and bandages, are currently being researched. See Matthew, T. L., et al. (1990) Ann. Surgery 50:40–44; Ochsner, M. G., et al. (1990) J. Trauma 30:884–887; Lerner, R. (1990) J. Surg. Res. 48:165–181; Lebowitz, R. A. et al. (1995) Am. J. of Otology 16:172–174; Suzuki, Y., et al. (1995) Arch. Surg. 130:952–955; and Rousou, J., et al. (1989) J. Thorac. Cardiovasc. Surg. 97:194–203.

Fibrinogen dressings were first used by trauma surgeons during World War I when Grey and his colleagues made prepolymerized fibrin sheets and powders. During World War II, fibrin glue was created with prepolymerized Styrofoam-like sheets of fibrin and fibrin films by the United States military and the American Red Cross. Fibrin based dressings show a significant difference in controlling bleeding time and reducing blood loss when compared to a control. See Jackson, M., et al. (1996) J. of Surg. Res. 60:15–22; and Jackson, M., et al. (1997) Surg. Forum, XL, VIII:770–772.

Despite the efficacy of fibrinogen dressings in controlling hemorrhage, the use of fibrinogen dressings was discontinued as blood and serum borne diseases such as hepatitis and HIV was often transmitted since the dressings comprised purified human or animal fibrinogen or other purified blood products. See Holcomb, J. B., et al. (1997) Surgical Clinics of North America 77:943–952. In the past few years, however, there has been a renewed interest in fibrin based products for treating wounds as plasma purification techniques have nearly eliminated the risk of blood and serum borne diseases. Additionally, suitable recombinant fibrinogen is expected to be commercially available soon.

There are a few patents that are directed to fibrinogen bandages, however, these fibrinogen bandages suffer from many drawbacks. The component that makes fibrinogen bandages too expensive for commercial use is the fibrinogen which is presently purified from human plasma and lyophilized onto a matrix which forms the backing of the bandage. The more fibrinogen that is added to the backing, the better the bandage works in stopping bleeding. However, the more fibrinogen added to the backing, the more costly the bandage. Additionally, the more fibrinogen added to the backing may contribute to the fragility of bandages having the higher amount of fibrinogen. The more fragile the bandage, the more difficult to work with as the bandage easily crumbles and does not bend to conform to various wound sites.

It has been speculated that the selective incorporation of agents that modify the biochemical pathways involved in clot formation will stabilize the formed clot and promote local coagulation. However, not all agents that normally promote clot formation and coagulation improve clot formation and coagulation when incorporated on or in fibrinogen dressings or bandages. For example, $\epsilon$-amino caproic acid which is an antifibrinolytic agent that impedes the destruction of fibrin by binding to the lysine binding sites of plasminogen would therefore be expected to provide a more stable clot. In fact, Amicar® is an $\epsilon$-amino caproic acid formulation used clinically whereby oral doses are used to control hemorrhaging after prostatectomies, to prevent rebleeding after dental extractions in patients having hereditary bleeding disorders, and to prevent rebleeding after subarachnoid hemorrhaging. However, it has been found that $\epsilon$-amino caproic acid incorporated in or on fibrinogen dressings or bandages actually decreased coagulation and clot formation as compared to fibrinogen bandages alone.

In addition, the quest to improve fibrinogen dressings or bandages and find suitable agents that promote coagulation and clot formation to be incorporated in or on the fibrinogen dressings has been hindered by the lack of an adequate arterial bleeding model. Prior art methods and models for studying clot formation and arterial bleeding have been inadequate as they do not provide a good control that may be standardized and used in comparative studies.

Thus, a need still exists for commercially viable and effective fibrinogen dressings or bandages and arterial bleeding models for the study of agents, methods, and devices that modulate coagulation and clot formation.

SUMMARY OF THE INVENTION

The present invention generally relates to fibrinogen wound dressings and methods of using thereof.

In some embodiments, the present invention provides a wound dressing comprising fibrinogen, fibrin, or both and at least one procoagulant. In some embodiments, the procoagulant is propyl gallate, gallic acid, or derivatives thereof, such as iso-propyl gallate, iso-butyl gallate, butyl gallate, iso-pentyl gallate, pentyl gallate, and lauryl gallate. In some embodiments, the procoagulant is a platelet-activating factor, such as thrombin, epinephrine, adenosine diphosphate, calcium, thromboxane, and the like, or a cellular component, such as collagen, fibronectin, and the like. In preferred embodiments, the wound dressing comprises propyl gallate in a therapeutic amount. The fibrinogen, fibrin, or both are preferably, mammalian, more preferably, human. Alternatively, the fibrinogen, fibrin, or both may be recombinant. In some embodiments, the procoagulant is lyophilized to a substrate, such as a piece of gauze or surgical mesh. In some embodiments, the procoagulant and the fibrinogen, fibrin, or both, are lyophilized together. In preferred embodiments, the wound dressing comprises fibrinogen in an amount of about 4.3 to about 6.7 mg/cm$^3$. The wound dressing may further comprise at least one pharmaceutical. Suitable pharmaceuticals include anti-inflammatory agents, analgesics, such as xylocaine and lidocaine, and antibiotics, such as gentimycin, vanomycin, ciprofloxacin, cefotetan, and penicillins. The wound dressings may further comprise a biological agent. Suitable biological agents include thrombin, stem cells, collagen, growth factors, such as epidermal growth factor, osteogenin, and somatomedin, and the like. The wound dressings may also comprise bio-absorbable components or a bio-absorbable matrix.

In some embodiments, the present invention provides a method of treating a wound comprising applying to the wound a wound dressing comprising fibrinogen, fibrin, or both and at least one procoagulant.

In some embodiments, the present invention provides a method of increasing an amount of or rate of coagulation of blood from a wound comprising applying to the wound a wound dressing comprising fibrinogen, fibrin, or both and at least one procoagulant.

In some embodiments, the present invention provides a method of activating a coagulation system of a subject comprising administering to the subject fibrinogen, fibrin, or both and at least one procoagulant.

In some embodiments, the present invention provides a method of increasing an amount of or rate of clot formation over a wound comprising applying to the wound a wound dressing comprising fibrinogen, fibrin, or both and at least one procoagulant.

In some embodiments, the present invention provides a method of increasing blood platelet counts in a subject comprising administering to the subject fibrinogen, fibrin, or both and at least one procoagulant.

In the methods of the present invention, the procoagulant is propyl gallate, gallic acid, or derivatives thereof, such as iso-propyl gallate, iso-butyl gallate, butyl gallate, iso-pentyl gallate, pentyl gallate, and lauryl gallate. The procoagulant may be a platelet-activating factor, such as thrombin, epinephrine, adenosine diphosphate, calcium, thromboxane, and the like, or a cellular component, such as collagen, fibronectin, and the like. In preferred embodiments, a therapeutic amount of propyl gallate is used, applied, or administered. The fibrinogen, fibrin, or both are preferably, mammalian, more preferably, human. Alternatively, the fibrinogen, fibrin, or both may be recombinant. In some embodiments, the procoagulant is lyophilized to a substrate, such as a piece of gauze or surgical mesh. In some embodiments, the procoagulant and the fibrinogen, fibrin, or both, are lyophilized together. In some embodiments, at least one pharmaceutical is used, applied, or administered. Suitable pharmaceuticals include anti-inflammatory agents, analgesics, such as xylocaine and lidocaine, and antibiotics, such as gentimycin, vanomycin, ciprofloxacin, cefotetan, and penicillins. In some embodiments, at least one biological agent, such as thrombin, stem cells, collagen, growth factor, osteogenin, and somatomedin, and the like, may be used, applied or administered. In some embodiments, the wound dressings may further comprise a bio-absorbable component or a bio-absorbable matrix.

In some embodiments, the present invention provides a method of studying arterial bleeding comprising scoring an arterial wall of a subject with a dermal punch and removing the scored tissue with a scissors. The subject is preferably a mammal, more preferably, a pig.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DESCRIPTION OF THE DRAWINGS

This invention is further understood by reference to the drawings wherein.

DETAILED DESCRIPTION OF THE INVENTION

Figure 1:
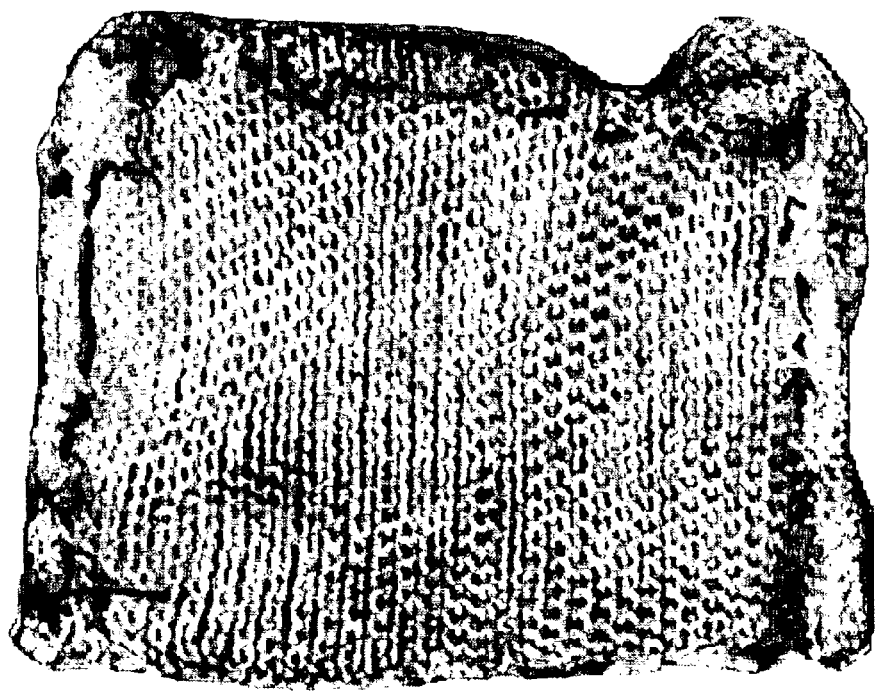
FIG. 1 is a photograph of the fibrinogen wound dressing preparation comprising propyl gallate in a pouch sewn on to a fibrinogen bandage.

The present invention relates generally to fibrinogen dressings or bandages that improve clot formation. The present invention provides fibrinogen dressings or bandages comprising agents that modulate the biochemical pathways involved in clot formation. In particular, the present invention provides fibrinogen dressings or bandages comprising procoagulant agents that promote coagulation locally and stabilize the newly formed clot. Additionally, the present invention relates to an arterial bleeding model for the study of agents, methods, and devices that affect arterial bleeding.

As used herein, "dressing" and "bandage" may be used interchangeably to refer to a device that may be used to cover, dress, protect, or heal a wound. As used herein, a "wound" includes damage to any tissue in a living organism. The tissue may be internal, external, or a combination thereof. The tissue may be hard or soft tissue. The wound includes any lesion resulting from an agent, injury, disease, infection, or surgical intervention. As described herein, fibrinogen bandages comprising collagen, fibrinogen, and thrombin obtained from Nycomed Austria GmbH were used. Specifically, the bandages used in the experiments herein comprise collagen layered with about 4.3 to about 6.7 mg/cm$^3$ of fibrinogen and about 1.5 to about 2.5 IU/cm$^2$ of thrombin. Although fibrinogen bandages from Nycomed Austria GmbH were used, other fibrinogen bandages known in the art may be used according to the present invention. See e.g. U.S. Pat. Nos. 4,453,939, 4,606,337, 5,942,278, and 6,177,126, and U.S. Patent Application Publication Nos. 20020015724 and 20020001624, which are herein incorporated by reference.

In preferred embodiments, the fibrinogen is human or recombinant, however, non-human fibrinogen may be used. Likewise, one of ordinary skill in the art will appreciate that the collagen, thrombin, or both may be non-human, human, or recombinant. Additionally, fibrin may be used in place of or in combination with fibrinogen. Therefore, fibrinogen, fibrin, or both may be used the dressings and methods of the present invention. However, fibrin is not preferred as it difficult to work with during bandage preparation. As used herein, "fibrinogen" may be used interchangeably with "fibrin".

The fibrinogen bandages of the present invention comprise at least one procoagulant. As used herein, "procoagulants" include any compound or composition that shifts the enzymatic equilibrium of the biochemical pathway or cascade involved in or related to coagulation from a resting state to an activated state. In preferred embodiments of the present invention, the fibrinogen bandages comprise propyl gallate, gallic acid, or derivatives thereof, such as iso-propyl gallate, iso-butyl gallate, butyl gallate, iso-pentyl gallate, pentyl gallate, and lauryl gallate. Procoagulants also include platelet-activating factors, such as thrombin, epinephrine, adenosine diphosphate, calcium, thromboxane, and the like, and cellular components, such as collagen, fibronectin, and the like. As described in the Examples below, the procoagulant, propyl gallate, was used in the form of Hemostatin™, which is available from Analytical Control Systems, Inc. (Fishers, Ind.). One will appreciate, however, that any composition comprising a procoagulant, such as propyl gallate, gallic acid, or derivatives thereof, may be used in accordance with the present invention so long as the composition lacks any agent, such as heparin or warfarin, which will significantly inhibit clotting. See e.g. U.S. Pat. Nos. 5,700,634, 5,451,509, and 5,709,889, which are herein incorporated by reference.

Preferably, the fibrinogen bandages of the present invention comprise a procoagulant in a therapeutic amount. As used herein, a "therapeutic amount" of a procoagulant is an amount that promotes blood coagulation, clot formation, or both. For example, a "therapeutic amount" of propyl gallate ranges from about 100 $\mu g/cm^2$ to about 3,000 $\mu g/cm^2$, preferably about 250 $\mu g/cm^2$ to about 2,000 $\mu g/cm^2$, more preferably about 500 $\mu g/cm^2$ to about 1,000 $mg/cm^2$ of the surface area of a wound. One of ordinary skill in the art may readily determine the optimal therapeutic amount of a given procoagulant with routine methods in the art.

As disclosed herein, the ability of fibrinogen bandages comprising propyl gallate to promote coagulation and scab formation was compared to fibrinogen bandages without propyl gallate in the arterial bleeding model described in the Examples below. Propyl gallate is commonly used in amounts that make it suitable as an emulsifier, preservative or antioxidant in pharmaceutical formulations. As an antioxidant, propyl gallate interferes with two critical oxygenase enzymes that produce stimulatory molecules in platelets, and thereby dampen the platelet response during clotting. As a procoagulant, propyl gallate appears to either induce apoptosis in platelets or rearrange the platelet cell membrane which expose lipid molecules, such as phosphatidylserine, needed in the coagulation biochemical cascade. See Nakagawa, Y., et al. (1997) Arch. Toxicol. 72(1):33–37; Qi, S. P., et al. (1993) Sci. China B. 36(6):702–709; and Serrano, A., et al. (1998) Arch. Biochem. Biophys. 350(1):49–54, which are herein incorporated by reference. Thus, prior to the present invention, it was questionable whether fibrinogen bandages comprising propyl gallate would promote coagulation and scab formation better than fibrinogen bandages alone.

Propyl gallate was added to fibrinogen bandages and then tested for hemostatic efficacy in the swine femoral artery bleeding model as described in the Examples below. For these studies, an injury was created in the femoral artery of a swine and blood loss was calculated by absorbing the blood on pre-weighed gauze. Two different fibrinogen+propyl gallate bandage preparations were used. The first preparation had a predetermined amount of propyl gallate sprinkled on top of the fibrinogen bandage and the second preparation had a predetermined amount of propyl gallate placed in a gauze-like pouch sewn on the fibrinogen bandage. Qualitatively, the animals treated with either preparation exhibited much more robust blood clotting at the surgical site. However, quantitatively the variability in the blood loss prevented a statistically significant result.

Although the preparations described in the specific Examples below comprise preparations having propyl gallate on the fibrinogen bandage and a preparation having a solution of propyl gallate lyophilized on a piece of gauze which was then attached on the fibrinogen bandage, other preparations are encompassed by the present invention. For example, a fibrinogen bandage within the scope of the present invention may include at least one procoagulant incorporated on the backing at the same time as the fibrinogen. Another preparation may include at least one layer of fibrinogen and at least one layer of at least one procoagulant. The fibrinogen bandage of the present invention may include at least one procoagulant homogenously dispersed throughout the fibrinogen. Alternatively, a solution of at least one procoagulant may be lyophilized on a carrier, such as a surgical mesh or a bio-absorbable matrix, and then placed on the fibrinogen bandage.

The two experiments, as described in the Examples below, that were conducted had two primary differences. In the first set of experiments, a skin biopsy punch was used to produced the arteriotomy. However, the arteriotomy produced in this manner was small and the edges were undefined. Additionally, since the bandage preparation having propyl gallate sprinkled on top of the fibrinogen bandage was used, it was unclear how much of the propyl gallate was contacted with the wound when the bandage was inverted and applied.

The results from these experiments mirrored this uncertainty. There was no statistical difference between the two treatments as the blood losses were 237.8±47.9 g, n=5 for the fibrinogen bandage alone and 315.3±111.5 g, n=6, (p=0.5) for the fibrinogen+propyl gallate as shown in Table 1.

TABLE 1

Blood loss following the femoral artery injury

|  | Blood Loss (g) | Bleeding Time (min) | Compressions |
|---|---|---|---|
| Fibrinogen bandage control 1st trial | 237.8 ± 47.9 | 14.7 ± 3.8 | 2.5 ± 0.3 |
| Fibrinogen bandage + PG 1st trial | 315.0 ± 111.5 p = 0.5 | 10.0 ± 2.0 p = 0.15 | 2.1 ± 0.3 |
| Fibrinogen bandage control 2nd trial | 563.0 ± 138.0 | 26.8 ± 6.3 | 7.2 ± 1.8 |
| Fibrinogen bandage + PG 2nd trial | 454.0 ± 86.0 p = 0.26 | 17.8 ± 1.8 p = 0.2 | 5.0 ± 0.9 p = 0.16 |

For the second set of experiments, the artery wall was scored first with the punch and then the tissue was removed with scissors. This resulted in a well-defined hole with clear-cut edges. The bandage preparation having the propyl gallate in the pouch sewn on the fibrinogen bandage was used. The blood loss from this injury was slightly higher than the first trial and this higher loss began to accentuate differences between the bandage treatments. Bleeding was reduced more using the fibrinogen+propyl gallate bandage as compared with the fibrinogen bandage alone. In this case, the blood loss with the fibrinogen bandage alone was 563.0 g±138.0 g, n=5 versus 454.0 g±86.0 g for the fibrinogen+propyl gallate bandage. However, there was still no statistically significant difference between the bandage either with or without the propyl gallate supplement (one tailed t-test, p=0.26). However, both experiments, the fibrinogen+propyl gallate bandages produced large, jelly-like clots (about 20 to about 30 ml) at the wound site which filled the arterial cut-down site. These jelly-like clots were not observed in the controls (fibrinogen bandage alone).

During the two sets of trials, in order to stop the bleeding and initiate clotting, pressure was manually applied to the wound site. After 2 minutes the pressure was removed to determine if the bleeding had stopped. If the bleeding had not stopped, pressure was reapplied. The cycles of pressure on and off were recorded and compared for the different treatments. While there was no significance difference in the number of compressions required for the fibrinogen bandage as compared to the fibrinogen+propyl gallate bandage (2.5±0.3 vs. 2.1±0.3, n=6) in the first set of experiments, the second set of experiments showed a difference. In the second set of experiments, the fibrinogen bandage alone required 7.2±1.8 compressions as compared to 5.0±0.9 compressions for the fibrinogen+propyl gallate bandage (p=0.16). This also translated into shorter bleeding times for animals treated with the fibrinogen+propyl gallate bandages (17.8 min±1.8 min) compared to the controls (26.8 min±6.3 min) (p=0.2). The second set of experiments showed that placing the propyl gallate in a pouch fixed to the fibrinogen bandage and scoring the arterial wall with the dermal punch and removing the tissue with scissors resulted in more consistent procedures and results.

To determine if the rapid hemorrhage was depleting coagulation factors and lowering platelet counts we measured fibrinogen levels, tested the activated partial thromboplastin time (aPTT) and prothrombin time (PT) and recorded the decrease in platelets during the experiments. To compare changes in parameters between bandage conditions and to eliminate interanimal variation, platelet counts, aPTT and PT were measured in blood samples taken at the start and end of each experiment and a score was calculated as a percent of the $t_0$ value.

The platelet counts decreased over the course of the bleeding period. The control, fibrinogen bandage alone, platelet value was 71.9%±3.0% and the fibrinogen+propyl gallate bandage value was 86.1%±1.8%. The control values were significantly lower than the fibrinogen+propyl gallate preparation (control vs. propyl gallate, p=0.07, n=4).

Similarly, the plasma concentration of fibrinogen decreased in the animals treated with the control bandages. Subjects treated with the fibrinogen bandage alone had a plasma fibrinogen concentration of 123.0 mg/dL±1.8 mg/dL (n=4) whereas subjects treated with the fibrinogen+propyl gallate bandage had a fibrinogen plasma concentration of 149.2 mg/dL±14.3 mg/dL (n=5).

When aPTT was assayed in blood samples drawn before and after the end of the experiment, the clotting time was shortened. This shortening of the aPTT occurred even in the presence of falling fibrinogen concentrations and dropping hematocrits. However, again the amplitude of the decrease was dependent on the treatment of the hemorrhage. The decrease in the aPTT was greater with the fibrinogen bandage alone (81.7%±5.8%, n=5) as compared with the fibrinogen+propyl gallate bandage (87.8%±3.8%, n=5). The p value for the fibrinogen+propyl gallate vs. fibrinogen control was only p=0.2. There was no change in PT for either the control bandages or the fibrinogen+propyl gallate bandages for the bandage preparations of Example 3, however, the bandage preparations of Example 4 did provide a significant difference.

It is well known that the amount of fibrinogen on the dressing surface is critical to the performance of fibrinogen dressings. Specifically, more fibrinogen yields a faster clotting time with less bleeding from the wound. However, fibrinogen is expensive and a large amount of fibrinogen on a bandage is difficult to use. Therefore, the present invention provides fibrinogen bandages comprising a procoagulant such as propyl gallate (PG). A fibrinogen bandage comprising a procoagulant may provide substantially the same result as a bandage using a greater amount of fibrinogen only. The present invention also provides methods of treating a wound comprising apply to the wound a fibrinogen bandage comprising a procoagulant.

As described herein, blood from wounds treated with a fibrinogen bandage comprising a procoagulant coagulated faster than blood from wounds treated with a fibrinogen bandage only. Additionally, the amount of clotted blood over wounds treated with a fibrinogen bandage comprising a procoagulant was greater than the amount of clotted blood over wounds treated with a fibrinogen bandage alone. Therefore, the present invention also provides methods of increasing the amount of or rate of coagulation of blood from a wound. The present invention also provides methods for increasing the amount of or rate of clot formation.

Also as described herein, the fibrinogen bandage of the present invention affected blood platelet and fibrinogen concentrations, and aPTT (clotting time). The mean percent decrease of platelet counts and fibrinogen concentrations in subjects treated with a fibrinogen bandage only was more than the decrease in counts and concentrations of subjects treated with a fibrinogen bandage comprising propyl gallate. In contrast, the mean aPTT clotting times in subjects treated with a fibrinogen bandage only was less than the concentrations in subjects treated with a fibrinogen bandage comprising propyl gallate. The in vitro aPTT assays are conducted last and indicates the activation state of proteins involved in the coagulation process. Therefore, a longer aPTT indicates that there is less systemic protein activation involved in coagulation when propyl gallate is present. These results indicate that a fibrinogen bandage comprising a procoagulant decreases the clotting time of a wound of a subject to as compared to the clotting time when a fibrinogen bandage alone is used, without causing systemic activation of the coagulation pathway. Additionally, these results indicate that the formation of the clot requires less of the coagulation proteins systemically (endogenous coagulation proteins). Therefore, the present invention provides methods for decreasing the clotting time of a wound of a subject. The present invention also provides methods for forming a clot in a subject using less endogenous coagulation protein.

Additionally, the fibrinogen bandages of the present invention may also include at least one pharmaceutical. Preferably, the pharmaceutical does not affect beneficial cellular functions and processes, such as platelet activation and coagulation. Preferably, the pharmaceutical does not adversely affect the performance, e.g. clotting enhancement, of the fibrinogen bandage. Suitable pharmaceuticals include anti-inflammatory agents, analgesics, such as xylocaine and lidocaine, and antibiotics, such as gentimycin, vanomycin, ciprofloxacin, cefotetan, and penicillins. The fibrinogen bandages of the present invention may further comprise a biological agent. Biological agents include thrombin, stem cells, collagen, growth factors, such as epidermal growth factor, osteogenin, and somatomedin, and the like. The fibrinogen bandages of the present invention may also comprise bio-absorbable components or a bio-absorbable matrix such as collagen and those described in U.S. Pat. Nos. 4,606,337, 6,056,970, and 6,197,325, which are herein incorporated by reference.

The fibrinogen bandages of the present invention are useful in the treatment of wounds, hemorrhages, burns and the like. Examples of wounds include those caused by lacerations, punctures, and surgery, such as those resulting from motorcycle accidents, and deep thoracic surgery. Clearly, the fibrinogen bandages of the present invention are useful for treating wounds having a large surface area and wounds that are difficult to suture or cauterize. The fibrinogen bandages are also useful for promoting healing of tissue grafts and burns.

The following examples are intended to illustrate but not to limit the invention. In the following examples, the fibrinogen bandages comprising equine collagen layered with about 4.3 to about 6.7 mg/cm$^2$ of fibrinogen and about 1.5 to about 2.5 IU/cm$^2$ of thrombin were used. The propyl gallate composition used was Hemostatin™ from Analytic Control Systems, Inc. (Fishers, Ind.).

The standards set forth in the "Guide for the Care and Use of Laboratory Animals" (NIH Publication 23–85) as promulgated by the committee on Care and Use of Laboratory Animals of the Institute of Laboratory Animal Resources, National Research Council were adhered to in conducting the experiments described herein.

EXAMPLE 1

Preparation of Fibrinogen Bandages 0.5 mg of propyl gallate was weighed and layered over the active surface of the fibrinogen bandage. See FIG. 1. In the first set of fibrinogen+propyl gallate bandage preparations, the propyl gallate was loosely sprinkled on the surface of the fibrinogen bandage. In the second set of fibrinogen+propyl gallate bandage preparations, the propyl gallate was placed in a small gauze-like pouch of surgical cellulose stitched to fibrinogen bandage. See FIG. 1. The control bandage did not have any propyl gallate. The fibrinogen bandage preparations were weighed, recorded, and placed on pre-weighed gauze. The gauze, not the bandage, was handled so as to avoid disturbing the prepared bandage.

EXAMPLE 2

Surgical Procedures

Animals used in the study were weighed and examined by a veterinarian and underwent about an 8 to about a 12 hour food restriction prior to surgery. On the day of the experiment, anesthesia was initiated with about 0.5 mg/kg IM Acepromazine sedative and about 0.4 mg/kg, IM atropine, followed by about 2 to about 4.4 mg/kg Telazol® (Tiletamine-Zolazepam) and about 2 to about 4.4 mg/kg Xylazine IM. The animals were intubated and placed on an automatic ventilator at settings of end tidal PCO2 of about 40 mmHg. Anesthesia was maintained with about 1.5 to about 1.8% isoflurane in 100% oxygen. Pulse oximetry, EtCO$_2$, EKG/BP and temperature (rectal) were monitored throughout the surgery. An arterial catheter was placed for blood pressure monitoring and for collection of arterial blood for blood gases and for coagulation tests. A venous catheter was placed for administration of resuscitation fluids.

Figure 3:
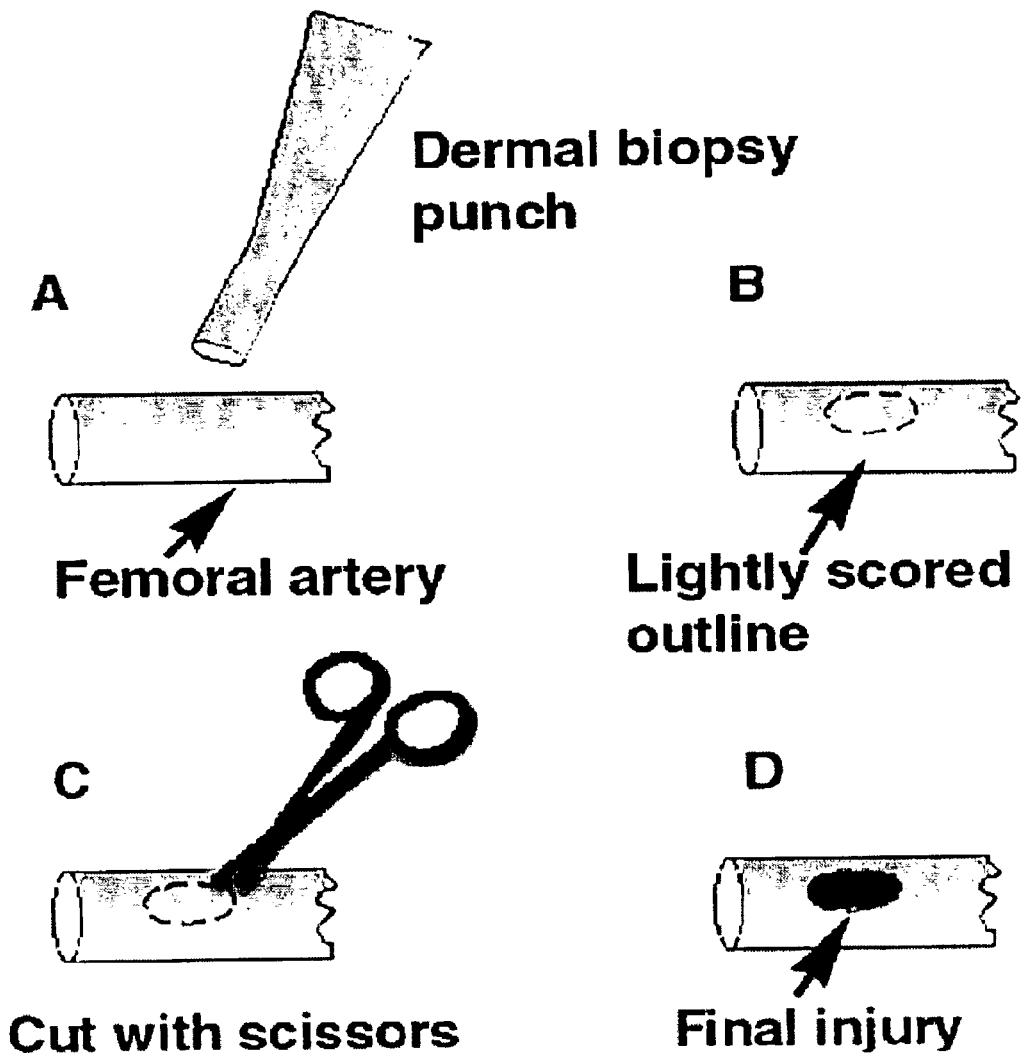
FIG. 3 is a schematic showing the procedure for puncturing the femoral artery of a subject.
Figure 4:
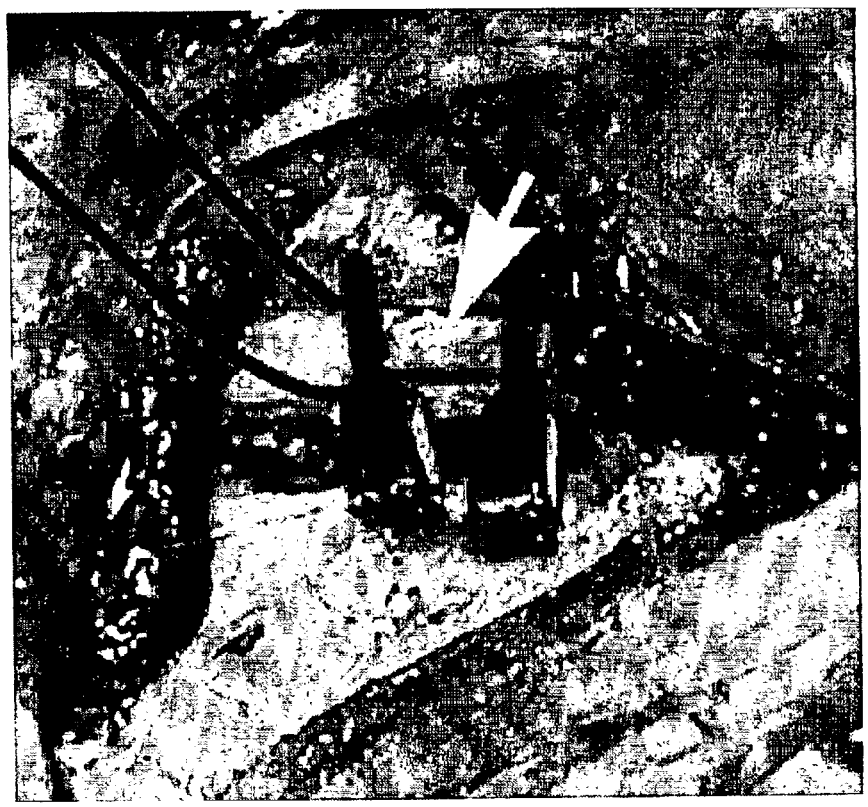
FIG. 4 is a picture of the preparation of the femoral arterial injury.

The femoral artery was isolated and umbilical ties were placed proximal and distal to the arteriotomy site for vessel orientation. Bull dog clamps were placed proximal and distal to the arteriotomy site to control for bleeding. A 2 mm diameter skin biopsy punch was used to make a reproducible injury. See FIG. 3 for schematic and FIG. 4 of an arteriotomy preparation. For the second set of the fibrinogen vs. fibrinogen+propyl gallate bandages (pouch formulation), the punch was used only to score the arterial wall to mark a template. Iris scissors were then used to create the actual hole. This approach eliminated the uncertainty of holes with hanging tissue or penetration through the full thickness of the artery. The injury was observed to bleed freely (about 2 seconds) and then a fibrinogen bandage or a fibrinogen+ propyl gallate bandage was applied to the arteriotomy site. Pressure on the bandage was applied manually for two continuous minutes. After two minutes, pressure was removed and pre-weighed gauze was used to absorb the blood from the wound. If bleeding continued after two minutes, pressure was reapplied for two minutes again. This cycle continued until bleeding ceased. The blood soaked gauze pads were weighed and the blood loss calculated.

During each experiment, blood pressure was monitored and if the subject's mean arterial pressure (MAP) dropped below 60 mmHg, resuscitation with warmed Ringer's Lactate was initiated to restore the MAP to 80 mmHg.

The experiment was designed to continue for 10 minutes after the end of bleeding or 1 hour. At the end of the bleeding period or one hour, the femoral artery was occluded, and all residual blood loss was evacuated and recorded. After the last set of measurements, the subject was euthanized with a lethal dose (1 ml/5kg) of Euthanasia-6 Solution C II (Veterinary Laboratory Inc, Lenexa, Kans.) injected via the ear vein catheter.

Blood gas analysis was performed on a Radiometer/ Copenhagen ABL 705 gas analyzer (Radiometer America, Inc., Westlake, Ohio) and coagulation functions (prothrombin time, activated partial thromboplastin time, thrombin time and fibrinogen concentration) were assayed on a STA4 Compac (Diagnostica Stago, Parsippany, N.J.). Complete blood counts were run on a Cell Dyne 1700 (Abbott Diagnostics, Abbott Park, Ill.).

Figure 5:
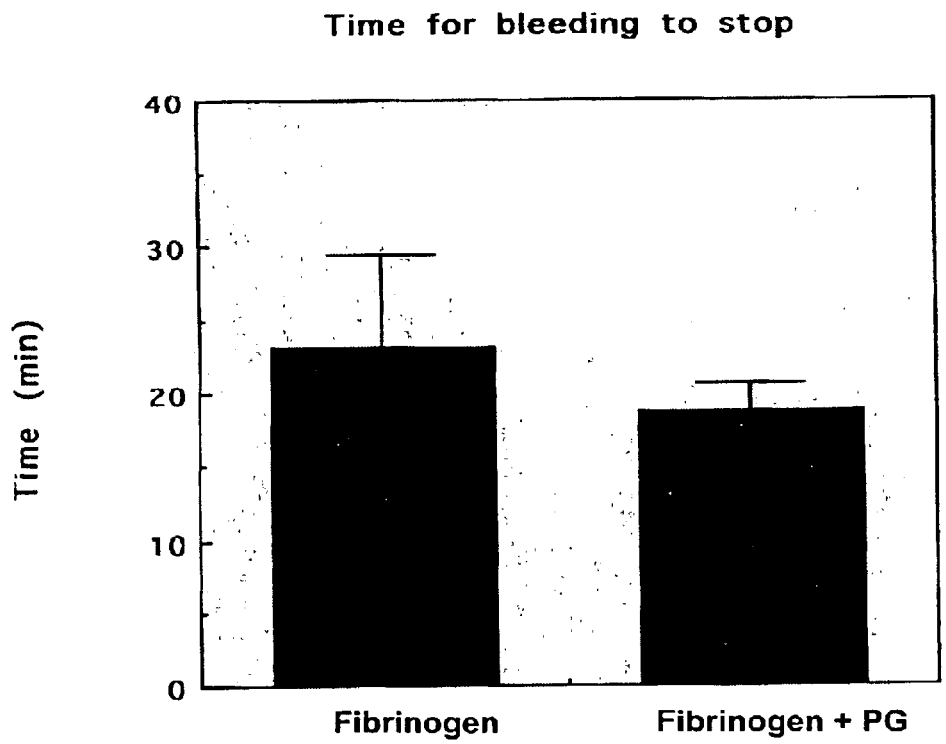
FIG. 5 is a graph comparing the time for bleeding to cessation following puncture of the femoral artery and application of each of the two bandages. Times are given in minutes and show the mean±SEM. Number of animals=5 per condition.

FIG. 5 is a graph comparing the time for bleeding to cessation following puncture of the femoral artery and application of each of the two bandages using conditions outlined for the second set of experiments. The injury was produced using the punch/scissors combination and the propyl gallate was contained in a pouch sewn to the bandage. Times are given in minutes and show the mean±SEM. Number of animals=5 per condition.

Figure 6:
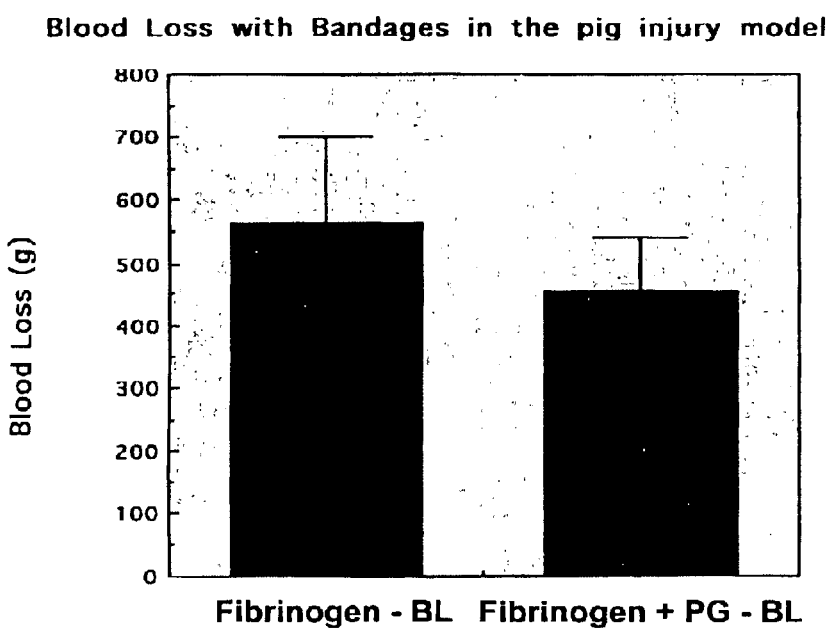
FIG. 6 is a graph comparing the blood loss following puncture of the femoral artery and application of each of the two bandages. Values are given in grams of blood and show the mean±SEM. Number of animals=5 per condition.

FIG. 6 is a graph comparing the blood loss following puncture of the femoral artery and application of each of the two bandages using conditions outlined for the second set of experiments. The injury was produced using the punch/ scissors combination and the propyl gallate was contained in a pouch sewn to the bandage. Values are given in grams of blood and show the mean±SEM. Number of animals=5 per condition.

Figure 7:
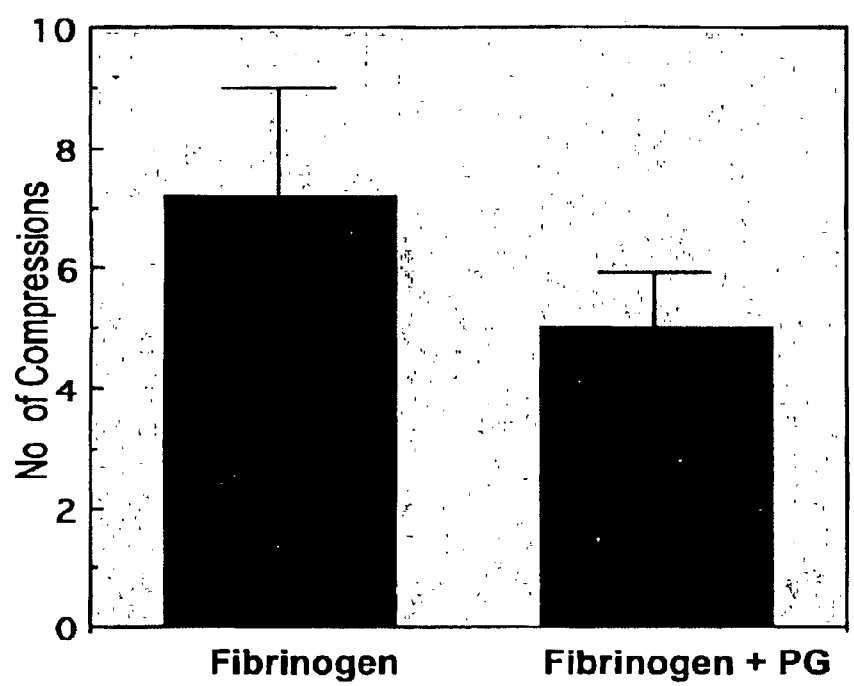
FIG. 7 is a graph comparing the number of compressions required to stop the bleeding following puncture of the femoral artery and application of each of the two bandages. Values are as compressions and show the mean±SEM. Number of animals=5 per condition.

FIG. 7 is a graph comparing the number of compressions required to stop the bleeding following puncture of the femoral artery and application of each of the two bandages using conditions outlined for the second set of experiments. The injury was produced using the punch/scissors combination and the propyl gallate was contained in a pouch sewn to the bandage. Values are as compressions and show the mean±SEM. Number of animals=5 per condition.

Differences between groups were analyzed using a unidirectional T-test assuming unequal variances. Values are expressed as means±the standard error. N values and p values are included with each measurement.

EXAMPLE 3

Assay for Changes in Coagulation Parameters and Platelet Counts During Arterial Bleeding To determine if the rapid hemorrhage was depleting coagulation factors and lowering platelet counts, fibrinogen levels were measured and the activated partial thromboplastin time (aPTT) and prothrombin time (PT) were determined. To compare changes in parameters between bandage conditions and to eliminate inter-animal variation, platelet counts, aPTT and PT were measured in blood samples taken at the start and end of each experiment and a score was calculated as a percent of the $t_0$ value.

It was found that the platelet counts decreased over the course of the bleeding period. The control, fibrinogen bandage alone, exhibited a platelet value of 71.9%±3.0% and the fibrinogen+propyl gallate bandage value was 86.1%±1.8%. Thus, the control value for the control was significantly lower than the fibrinogen+propyl gallate bandage (control vs. PG, p=0.07, n=4).

Similarly, the plasma concentration of fibrinogen decreased in the subjects treated with the control bandages, fibrinogen bandage alone. At the end of the experiment, subjects treated with the control exhibited a fibrinogen concentration of 123.0 mg/dL±1.8 mg/dL (n=4). Subjects treated with the fibrinogen bandage+propyl gallate exhibited a fibrinogen concentration of 149.2 mg/dL±14.3 mg/dL (n=5).

When aPTT was assayed in blood samples drawn before and after the end of the experiment, it was discovered that the clotting time was shortened. This shortening of the aPTT occurred even in the presence of falling fibrinogen concentrations and dropping hematocrits. However, again the amplitude of the decrease was dependent on the treatment of the hemorrhage. The fibrinogen bandage alone produced a greater decrease in the aPTT (81.7%±5.8%, n=5) than the fibrinogen bandage+propyl gallate (87.8%±3.8%, n=5). The p value for fibrinogen bandage vs. fibrinogen bandage+propyl gallate was only p=0.2. There was no change in PT for either the fibrinogen bandage alone or the fibrinogen+propyl gallate bandage.

EXAMPLE 4

Lyophilized Propyl Gallate Mesh Fibrinogen Bandages

A. Bandage Preparation

Figure 2:
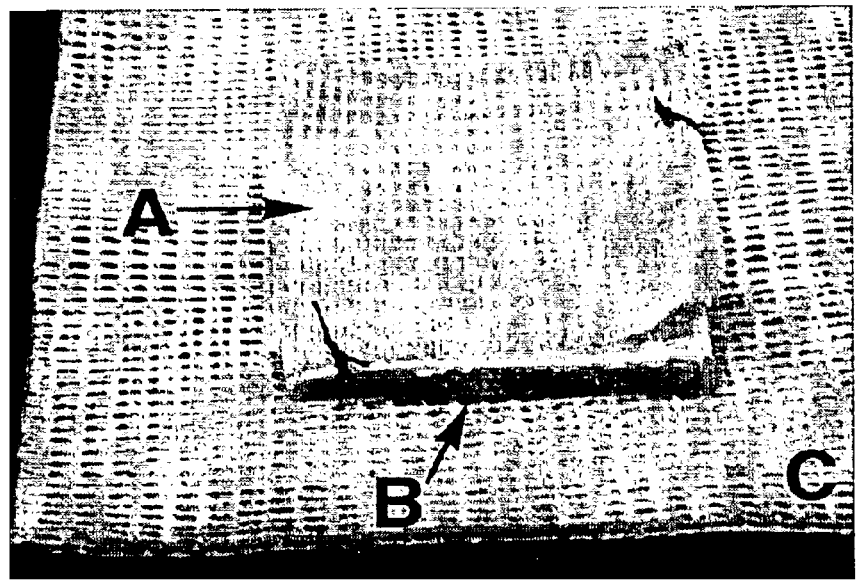
FIG. 2 is a photograph of the fibrinogen wound dressing preparation comprising propyl gallate that was dissolved and then freeze-dried (lyophilized) onto a gauze bandage that was then attached to a fibrinogen bandage.

Prior to making the arteriotomy, a propyl gallate (PG) composition was dissolved in 100 mM NaOH (1.0 g/10 mL) and 3 mL of the solution was added to a 4×4 cm gauze (Mirasorb sponge, Johnson and Johnson Medical, Arlington, Tex.). The wet gauze was lyophilized in a DuraDry/DuraStop Lyophilizer (FTS Sytems, Stoneridge, N.Y.) by cooling the samples to −40° C. and then drying at 50 mTorr. The resulting product comprised the propyl gallate composition adhered to the mesh of the gauze but did not completely occlude the openings of the mesh. The lyophilized product was stored in a dessicator until immediately before the procedure. At that time, the gauze with lyophilized propyl gallate composition was gently sutured at two opposite corners to the active surface of a 4×4 cm square of a fibrinogen bandage. See FIG. 2. The bandage preparation was weighed, recorded and placed on pre-weighed gauze. The gauze (not the bandage) was handled to avoid disturbing the prepared bandage.

B. Surgical Procedures

Anesthesia. Sixteen male Yorkshire pigs 19.4 kg (±1.57 kg) were administered acepromazine (0.5 mg/kg) and atropine (0.04 mg/kg) intramuscularly as a pre-anesthetic. Pigs were then administered Telazol (tiletamine-zolepam) (3 mg/kg) and xylazine (3 mg/kg) intramuscularly for induction of anesthesia. Anesthesia was maintained with about 1.5 to about 1.8% isoflurane in 100% oxygen. Respiration was controlled by a pressure ventilator sustaining an end tidal $PCO_2$ ($EtCO_2$) of about 45 mmHg. Anesthesia was monitored in accordance with the American Society of Anesthesiologists standards including pulse oximetry, $EtCO_2$, EKG/BP, and temperature (rectal). A peripheral intravenous catheter was placed percutaneously into an auricular vein for administration of resuscitation fluids. A vascular catheter was placed percutaneously into an auricular artery for blood pressure monitoring and for collection of arterial blood for blood gases and for coagulation tests.

Technique. Anesthetized pigs were placed in dorsal recumbency. Hair was clipped from the left inguinal area. The clipped region was cleansed with a chlorhexidine gluconate scrub and isopropyl alcohol. The femoral artery was surgically isolated and umbilical tape ties were placed proximal and distal to the arteriotomy site for vessel orientation. Bull dog clamps were placed proximal and distal to the arteriotomy site to control for bleeding. A 2 mm skin biopsy punch was used to score the arterial wall to mark a template. Iris scissors were then used to create the actual hole. This approach made a reproducible hole of about 1×2 mm without the uncertainty of irregular holes, hanging tissue flaps or penetration through the full thickness of the artery by the biopsy punch. The bulldog clamps were released and the injury was observed to bleed freely (about 2 sec). One of two randomly assigned hemostatic bandages was then applied to the arteriotomy site. Pressure on the dressing was applied manually for two continuous minutes.

In all experiments, the same investigator performed the arteriotomy and the same investigator applied the pressure to the wound to ensure consistency. After two minutes, pressure was removed and pre-weighed gauze was used to absorb the blood from the wound. If bleeding continued after two minutes, manual pressure was reapplied for two minutes. This cycle continued until bleeding ceased. The blood soaked gauze pads were weighed and the blood loss calculated.

During the experiment, blood pressure was monitored and if the subject's mean arterial pressure (MAP) dropped below 60 mmHg, resuscitation with warmed Ringer's Lactate was initiated to restore the MAP to at least 60 mmHg.

The experiment was designed to continue for 10 minutes after the end of bleeding or 30 min. At the end of the bleeding period or 30 min, the femoral artery was occluded, and all residual blood loss was recorded. The bleeding time was recorded from the release of the clamps to the cessation of bleeding. After the last set of measurements, the animal was euthanized with a lethal dose (1 ml/5kg) of Euthanasia-6 Solution C II (Veterinary Laboratory Inc, Lenexa, Kans.) injected via the ear vein catheter.

C. Measurement of Hematological Parameters

Blood gas analysis was performed on a Radiometer/Copenhagen ABL 705 gas analyzer (Radiometer America, Inc, Westlake Ohio) and coagulation functions (prothrombin time, activated partial thromboplastin time, thrombin time and fibrinogen concentration) were assayed on a STA Compact (Diagnostica Stago, Parsippany, N.J.,). Complete blood counts were run on a Cell Dyne 1700 (Abbott Diagnostics, Abbott Park Ill.).

D. Results

The blood loss was 251.0±66.5 g for the fibrinogen bandage alone, n=12 versus 121.0±40.7 g, n=13 for fibrinogen+PG bandages, p=0.05. Thus, bleeding was reduced in the propyl gallate treated bandage set. Additionally, the injury sites of the animals treated with the fibrinogen+PG bandages contained large, jelly-like clots (about 20 to about 30 ml) filling the arterial cut-down site that were not observed in the control conditions.

As shown in Table 2, there was a slight but significant difference in the number of compressions required for the fibrinogen bandage as compared to the fibrinogen+propyl gallate bandage (3.25±0.5 v. 1.91±0.3, n=12, p=0.02) which also translated into shorter bleeding times for animals treated with fibrinogen+PG bandages (6.4 min±1.3 min) compared to the fibrinogen bandage controls (13.2 min±2.5 min) (p=0.01).

TABLE 2

Blood loss following the femoral artery injury

|  | Blood Loss (g) | Bleeding Time (min) | Number of Compressions |
|---|---|---|---|
| Fibrinogen control | 251.8 ± 66.5 | 13.2 ± 2.5 | 3.25 ± 0.5 |
| Fibrinogen + PG | 121.0 ± 40.7 | 6.4 ± 1.3 | 1.91 ± 0.3 |
|  | p = 0.05 | p = 0.01 | p = 0.01 |
|  | n = 12 | n = 12 | n = 12 |

Hemorrhage parameters are expressed as means ± SEM.
P values are calculated between control values and experimental conditions using a one-tailed t-test.

As would be expected, with the shorter bleeding times, the animals treated with fibrinogen+PG bandages required less resuscitation fluid (619.2±109.6 ml, n=13 than the animals treated with the control bandages (900.0±99.0 ml, p=0.03)

To determine if the rapid hemorrhage was depleting coagulation factors and lowering platelet counts, the fibrinogen levels were measured, and the activated partial thromboplastin time (aPTT) and prothrombin time (PT) were tested, and the decrease in platelets during the experiments was recorded. To compare changes in parameters between bandage conditions and to eliminate inter-animal variation, platelet counts, aPTT and PT were measured in blood samples taken at the start and end of each experiment and a score was calculated as a percent of the initial value.

The platelet counts decreased for both conditions over the course of the bleeding period with the controls showing a higher decline. The fibrinogen bandage control platelet value was 71.9%±3.0% of starting values while the fibrinogen+PG bandage value was 86.1%±1.8% (p=0.003, n=5). See Table 3.

TABLE 3

Coagulation parameters following femoral artery injury

|  | Platelet counts (%) | Fibrinogen (mg/dL) | aPPT (%) |
|---|---|---|---|
| Fibrinogen control | 71.9 ± 3.0 | Initial 187.6 ± 15.7 Final 160.8 ± 12.0 | 81.7 ± 5.8 |
| Fibrinogen + PG | 86.1 ± 1.8 | Initial 189.5 ± 9.9 Final 164.1 ± 8.9 | 87.8 ± 3.8 |
|  | p = 0.003 | p = NS | p = NS |
|  | n = 5 | n = 11 | n = 5 |

Platelet counts and aPPT are shown as percent initial value ($t_{end}/t_0 \times 100$).
Fibrinogen is shown as the concentration at the time bleeding stopped.
P values for fibrinogen were not significant (NS) when calculated within groups (initial vs. final concentration) or between experimental (Fibrinogen vs PG/fibrinogen).

The plasma concentration of fibrinogen decreased slightly but not significantly in both sets of animals and there were no significant differences between the two groups of animals. See Table 2.

When aPTT was assayed in blood samples drawn before and after the end of the experiment, the clotting time was shortened. This shortening of the aPTT occurred even in the presence of falling fibrinogen concentrations and dropping hematocrits. However, the decrease in the aPTT in the fibrinogen control bandages (81.7%±5.8%, n=5) compared to fibrinogen+PG bandages (87.8%±3.8%, n=5) was not statistically significant (p value=0.2). In contrast to the decrease in aPTT, there was no observable change in the PT for either the fibrinogen control bandages or the fibrinogen+propyl gallate bandages.

When compared with the other propyl gallate preparations, the results indicate that the closer association between the lyophilized propyl gallate on the gauze and the fibrinogen bandage provide better results. Thus, additional preferred embodiments include preparations wherein the fibrinogen and the coagulation components are combined and lyophilized together as a single layer of mixed components on a bandage.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A wound dressing comprising fibrinogen, fibrin, or both and a therapeutic amount of propyl gallate.

2. The wound dressing of claim 1, wherein the fibrinogen is human.

3. The wound dressing of claim 1, wherein the fibrin is human.

4. The wound dressing of claim 1, wherein the fibrinogen is in an amount of about 4.3 to about 6.7 mg/cm$^3$.

5. The wound dressing of claim 1, further comprising collagen.

6. The wound dressing of claim 1, further comprising thrombin.

7. The wound dressing of claim 1, further comprising at least one pharmaceutical.

8. The wound dressing of claim 7, wherein the pharmaceutical is an analgesic, an anti-inflammatory agent, or an antibacterial.

9. The wound dressing of claim 1, further comprising a biological agent.

10. The wound dressing of claim 1, further comprising a bio-absorbable component or a bio-absorbable matrix.

11. The wound dressing of claim 10, wherein the bio-absorbable component or the bio-absorbable matrix comprises collagen.

12. The wound dressing of claim 1, wherein the procoagulant is lyophilized to a substrate.

13. The wound dressing of claim 1, wherein the fibrinogen, fibrin, or both and the procoagulant are lyophilized together.

14. A method of treating a wound comprising applying to a wound a wound dressing comprising fibrinogen, fibrin, or both and a therapeutic amount of propyl gallate.

15. The method of claim 14, wherein an amount of or rate of coagulation of blood from the wound is increased.

16. The method of claim 14, wherein an amount of or rate of clot formation over the wound is increased.

17. The method of claim 14, wherein blood platelet counts in the subject are increased.

* * * * *